(12) United States Patent
Hipp et al.

(10) Patent No.: US 7,883,847 B2
(45) Date of Patent: Feb. 8, 2011

(54) TRANSCRIPTIONAL PROFILING OF STEM CELLS AND THEIR MULTILINEAGE DIFFERENTIATION

(75) Inventors: Jason Hipp, Fountain Valley, CA (US); Shay Soker, Greensboro, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 484 days.

(21) Appl. No.: 11/394,766

(22) Filed: Mar. 31, 2006

(65) Prior Publication Data

US 2006/0246488 A1    Nov. 2, 2006

Related U.S. Application Data

(60) Provisional application No. 60/667,497, filed on Apr. 1, 2005.

(51) Int. Cl.
    *C12Q 1/68* (2006.01)
(52) U.S. Cl. ............................................. 435/6; 435/4
(58) Field of Classification Search ........................ None
    See application file for complete search history.

(56) References Cited

U.S. PATENT DOCUMENTS

| | | | |
|---|---|---|---|
| 5,843,780 A | 12/1998 | Thomson | |
| 6,200,806 B1 | 3/2001 | Thomson | |
| 6,777,231 B1 | 8/2004 | Katz et al. | |
| 7,015,037 B1 * | 3/2006 | Furcht et al. | 435/372 |
| 2002/0182728 A1 | 12/2002 | Ramiya et al. | |
| 2003/0180269 A1 | 9/2003 | Hariri | |
| 2005/0124003 A1 * | 6/2005 | Atala et al. | 435/7.2 |

FOREIGN PATENT DOCUMENTS

WO    WO 03-042405 A2    5/2003

OTHER PUBLICATIONS

Lefevre et al. Arch Biochem Biophys 1999;368:329-37.*
Levy et al. Differentiation 1982;22:12-8.*
Teramoto et al. J Hepatob Pancreat Surg 2005;12:196-202.*
Yachnin et al. PNAS 1984;81:894-7.*
Stange et al. Biochim Biophys Acta 1981;663:613-20.*
Shirahashi et al. Cell Transplant 2004;13:197-211.*
Roglans et al. Clin Pharmacol Ther 2000;72:692-701.*
Cohen et al. Biochem Pharmacol 1993;45:2203-8.*
Laurson et al. Int J Exp Path Feb. 2005;86:1-18.*
Seo et al. Biochem Biophys Res Comm Mar. 2005;328:258-64.*
International Preliminary Report on Patentability, Search Report and Written Opinion, PCT/US2006/012018, mailed Jan. 10, 2008.
International Search Report and Written Opinion, PCT/US2006/012018, mailed Nov. 26, 2007.
Hipp J D et al. Transcriptional profiling of pluripotent progenitor cells from human amniotic fluid. FASEB Journal (Mar. 7, 2005), vol. 19, No. 5, Suppl. S, Part 2, pp. A1311.
Jessen B A et al. Expression profiling during adipocyte differentiation of 3T3-L1 fibroblasts. Gene (2002), vol, 299, pp. 95-100.
Gomez F E et al. Molecular differences caused by differentiation of 3T3-L1 preadipocytes in the presence of either dehydroepiandrosterone (DHEA) or 7-oxo-DHEA. Biochemistry (2002), vol. 41, 5473-5452.
Kim Y-C et al. Regulation of stearoyl-CoA desaturase genes: role in cellular metabolism and preadipocyte differentiation. Biochemical and Biophysical Research Communications (1999), vol. 266, pp. 1-4.
Gomez F E et al. Effects of serculic acid on stearoyl-CoA desaturase in differentiating 3T3-L1 adipocytes. Biochemical and Biophysical Research Communications (2003), vol. 300, pp. 316-326.
Kehat I et al. Human embryonic stem cells can differentiate into myocytes with structural and functional properties of cardiomyocytes. The Journal of Clinical Investigation. Aug. 2001; 108(3): 407-414.
Ginis I et al. Differences between human and mouse embryonic stem cells Developmental Biology. 2004; 269-380.
Mestas J and Hughes CCW. Of mice and not men: differences between mouse and human immunology. The Journal of Immunology. 2004. 172: 2731-2738.

* cited by examiner

*Primary Examiner*—Q. Janice Li
(74) *Attorney, Agent, or Firm*—Myers Bigel Sibley & Sajovec, P.A.

(57) ABSTRACT

The present invention concerns methods of screening cells for differentiation or de-differentiation, and/or for status as a pluripotent or multipotent (e.g., "stem") cell, by detecting the differential expression (e.g., upregulation, downregulation) of genes.

7 Claims, 3 Drawing Sheets

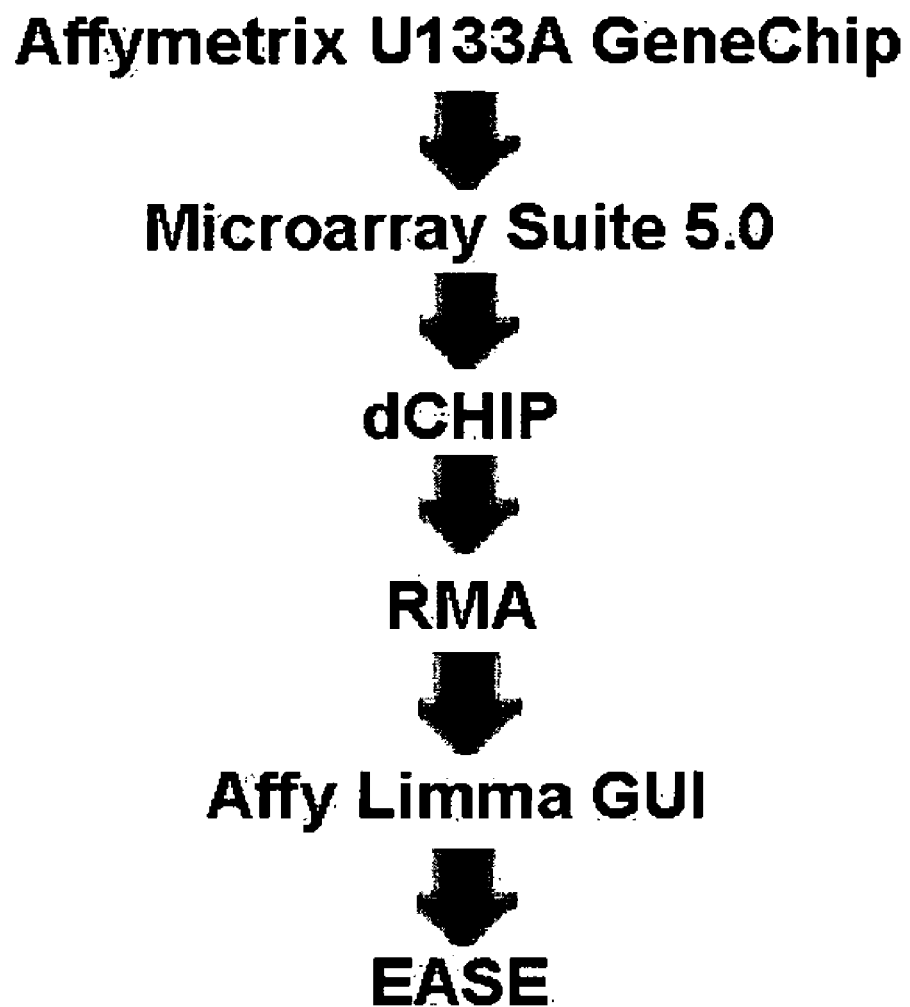
Figure 1: Methodology for microarray analysis.

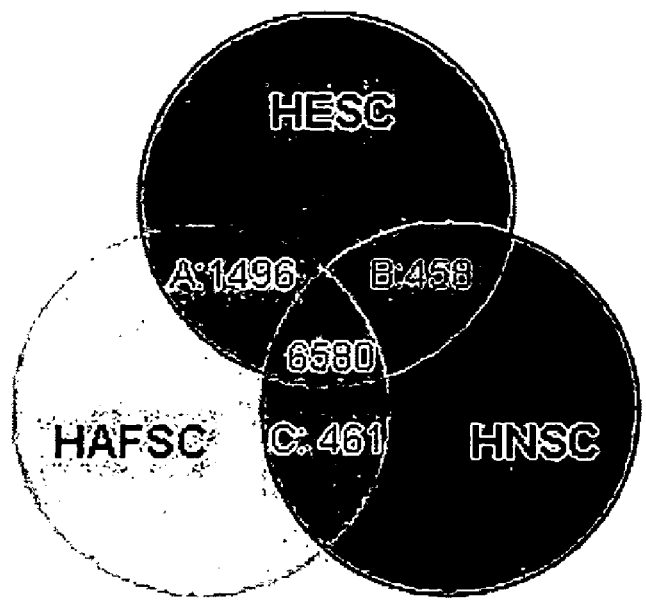
Figure 2a: Venn diagram comparison of genes present in HAFSC, HESC, and HNSC.
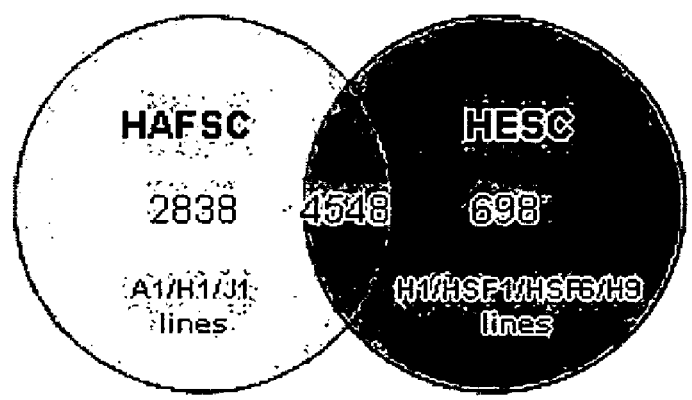
Figure 2b: Venn diagram comparison of 3 genetically distinct HAFSC lines and 4 genetically distinct lines.

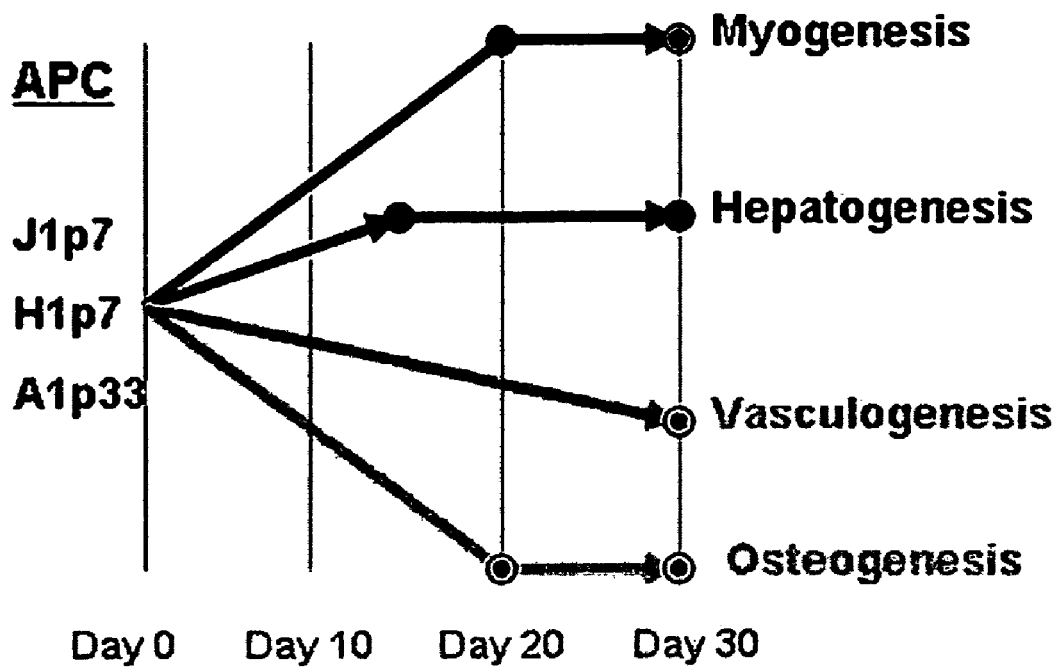
Figure 3a: Time-points and lineages profiled by microarrays.
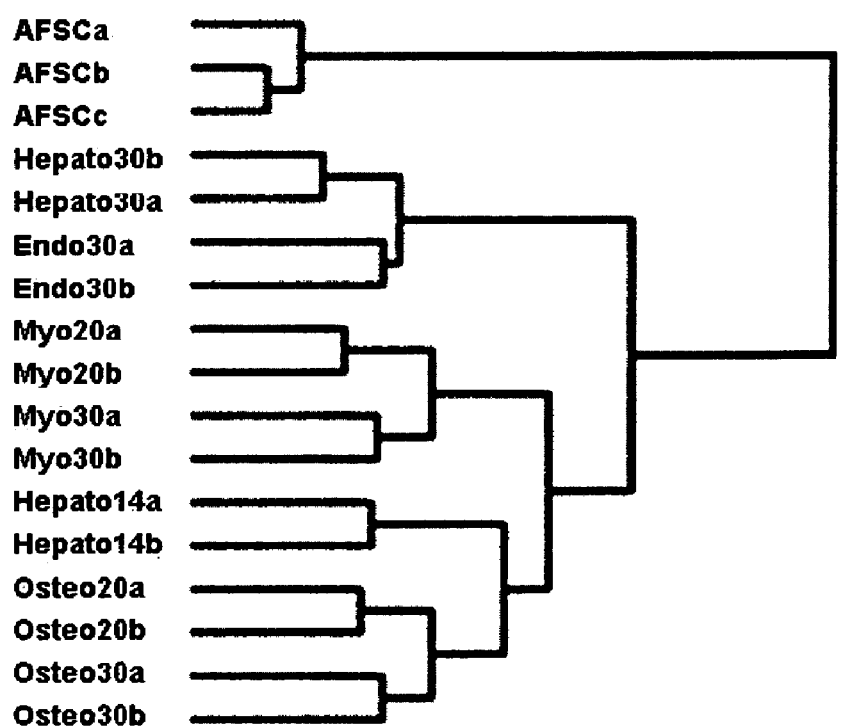
Figure 3b: Hierarchical clustering of all microarray data.

US 7,883,847 B2

TRANSCRIPTIONAL PROFILING OF STEM CELLS AND THEIR MULTILINEAGE DIFFERENTIATION

RELATED APPLICATIONS

This application claims the benefit of U.S. Provisional Patent Application No. 60/667,497, filed Apr. 1, 2005, the disclosure of which is incorporated by reference herein in its entirety.

FIELD OF THE INVENTION

The present invention concerns the detection of differentiation of pluripotent or multipotent cells into lineage specific cells, the ability to de-differentiate lineage-specific cells into pluripotent or multipotent cells, and cDNAs and kits useful for carrying out such methods.

BACKGROUND OF THE INVENTION

The ideal resource for tissue engineering applications is an immunocompatible and pluripotential cell, capable of differentiating into tissues of all three germ layers. Human pluripotential cells can be created using In vitro fertilization technologies (human embryonic stem cells, HESC) [1], from parthenogenesis the chemical activation of human oocytes (parthenogentically derived embryonic stem cells, PGESC) [2] [3], from isolated human germ cells (primordial germ cells, PGC) [4], or from human amniotic fluid (human amniotic fluid derived stem cells, HAFSC). The advantages of HAFSC are their isolation efficiency, expansion potential and their immunocompatibility, thus, not requiring patients to undergo high dose immunosuprressants to prevent immune rejection during cell transplantation.

HAFSC can be isolated from amniotic fluid between 14-18 weeks of gestation and comprise approximately 0.8% to 1.4% of the cells present in amniotic fluid (in submission). These cells are grown in basic medium supplemented with serum, have a high self renewal capacity (>300 population doublings), with a doubling time of less than 36 hours, do not require a feeder layer for undifferentiated expansion, and are autologus with the fetus. In addition, HAFSC maintain their telomeres and normal karyotpye throughout late passaging. Early passage HAFSC express SSEA-4 and OCT-4, but not the full complement of markers expressed by HESC (TRA 1-60, TRA1-81). While they are capable of forming embryoid like bodies, they do not form teratomas when injected into SCID mice. HAFSC can be differentiated in vitro into bone, muscle, fat, endothelia, liver and neurons. When mouse chimeras were created by injecting AFSC into blastocysts, AFSC derived cells were found throughout the embryo.

SUMMARY OF THE INVENTION

A first aspect of the present invention is a method of screening a pluripotent or multipotent cell for differentiation into a (i) heptogenic, (ii) myogenic, (iii) osteogenic, or (iv) endothelial specific cell line, comprising:

(a) providing a cell for which differentiation is to be determined, then (b) optionally, but in some embodiments preferably, subjecting the cell to differentiating conditions; and then (c) detecting in the cell differential expression of: (i) at least one, two, three or four hepatogenic specific genes such as described herein, including for example those selected from the group consisting of stearlyl-CoA desaturase (SCD), 3-hydroxy-3-methylglutaryl-Coenzyme A reductase (HMGCR), insulin inducd gene 1 (INSIG1), chromosome 20 open reading frame 97 (C20orf97), lipase A (LIPA), fatty acid desaturase 1 (FADS1), 7-dehydrocholesterol reductase (DHCR7), apolipoprotein D (APOD), squalene epoxidase (SQLE), cholesterol 25-hydroxylase (CH25H), lipin 1 (LPIN1), insulin induced gene 1 (INSIG1), flavin cntaining monooxygenase 1 (FMO1), aldo-keto reductase family 1 member 1C (AKR1C1), insulin-like growth factor 2 receptor (IGFR2R), ATP-binding cassette sub-family A member 1 (ABCA1), X-box binding protein 1 (XBP1) and mucin 1 (MUC1);

(ii) at least one, two, three or four myogenic specific genes as described herein, including for example those selected from the group consisting of insulin-like grwth factor binding protein 3 (IGFBP3), caldesmonin 1 (CALD1), a disintegrin and metallproteinase domain 12 (ADAM12), transglutaminase 2 (TGM2), tumor necrosis factor receptor superfamily member 11b (TNFRSF11B), protein kinase H11 (H11), cardiac muscle alpha actin (ACTC), and sarcoglycan delta (SGCD); at least one osteogenic specific gene selected from the group consisting of: intracellular adhesion molecule 1 (ICAM1), osteomodulin (OMD), tissue inhibitor of metalloporteinase 4 (TIMP4), sex determining region Y box 4 (SOX4), secreted phosphoprotein 1 (SPP1), v-fos FBJ murine osteosarcoma viral oncogene homolog (FOS), alpha V integrin (ITGAV), prolactin (PRL), alpha 4 integrin (ITGA4), peroxisome proliferative activated receptor gamma (PPARG), secreted protein acidic cystein-rich (SPARC) sarcoma amplified sequence (SAS), and bone morphogenetic protein 1 (BMP1), (iii) at least one, two, three or four osteogenic specific genes as described herein, including for example those selected from the group consisting of: intracellular adhesion molecule 1 (ICAM1), osteomodulin (OMD), tissue inhibitor of metalloproteinase 4 (TIMP4), sex determining region Y box 4 (SOX4), crystalin alpha B (CRYAB), secreted phosphoprotein 1 (SPP1), v-fos FBJ murine steosarcoma viral oncogene homolog (FOS), alpha V integrin (ITGAV), prolactin (PRL), alpha 4 integrin (ITGA4), peroxisome proliferative activated receptor gamma (PPARG), secreted protein, acidic, cystein-rich (SPARC), sarcoma amplified sequence (SAS), and bone morphogenetic protein 1 (BMP1), or (iv) at least one, two, three or four endothelial specific genes as described herein, including for example those selected from the group consisting of pentaxin-related gene rapidly induced by IL-1 beta (PTX3), selenprotein P plasma 1 (SEPP1), tissue factor pathway inhibitor (TFP1), angiopietin 1 (ANGPT1), angiopoietin-like 2 (ANGPTL2), 3-hydroxy-3-methylglutaryl-Coenzyme A reductase (HMGCR), kruppel-like factor 4 (KLF4), endothelial differentiation lysophosphatidic acid G-protein coupled receptor 2 (EDG2), matrix metalloporiteinase 14 (MPP14), neronal cell adhesion molecule (NRCAM), interleukin 6 (IL6), and tumor necrosis factor, alpha-induced protein 6 (TNFAIP6);

wherein (i) upregulation of expression of the at least one, two, three or four hepatogenic specific genes indicates differentiation of the cell into a heptogenic specific cell line, (ii) upregulation of expression of the at least one, two, three or four myogenic specific gene indicates differentiation of the cell into a myogenic specific cell line, (iii) upregulation of expression of the at least one, two, three or four osteogenic specific genes indicates differentiation of the cell into an osteogenic specific cell line, or (iv) upregulation of the expression of the at least one, two, three or four endothelial specific genes indicates differentiation of the cell into and endothelial specific cell line.

A second aspect of the present invention method of screening a cell such as a (i) heptogenic, (ii) myogenic, (iii) osteogenic, or (iv) endothelial specific cell for de-differentiation into a pluripotent or multipotent cell or stem cell (e.g., determining "sterness" of the cell), comprising:

(a) providing a cell such as a pluripotent or multipotent cell for which de-differentiation is to be determined, then (b) optionally, but in some embodiments preferably, subjecting the cell to de-differentiating conditions; and then (c) detecting in the cell downregulation of a downregulated or universally downregulated gene as described herein, and/or differential expression of: (i) at least one, two, three or four hepatogenic specific genes such as described herein, including for example those selected from the group consisting of stearlyl-CoA desaturase (SCD), 3-hydroxy-3-methylglutaryl-Coenzyme A reductase (HMGCR), insulin inducd gene 1 (INSIG1), chromosome 20 open reading frame 97 (C20orf97), lipase A (LIPA), fatty acid desaturase 1 (FADS1), 7-dehydrocholesterol reductase (DHCR7), apolipoprotein D (APOD), squalene epoxidase (SQLE), cholesterol 25-hydroxylase (CH25H), lipin 1 (LPIN1), insulin induced gene 1 (INSIG1), flavin cntaining monooxygenase 1 (FMO1), aldo-keto reductase family 1 member 1C (AKR1C1), insulin-like growth factor 2 receptor (IGFR2R), ATP-binding cassette sub-family A member 1 (ABCA1), X-box binding protein 1 (XBP1) and mucin 1 (MUC1);

(ii) at least one, two, three or four myogenic specific genes such as described herein, including for example those selected from the group consisting of insulin-like grwth factor binding protein 3 (IGFBP3), caldesmonin 1 (CALD1), a disintegrin and metallproteinase domain 12 (ADAM12), transglutaminase 2 (TGM2), tumor necrosis factor receptor superfamily member 11b (TNFRSF11B), protein kinase H11 (H11), cardiac muscle alpha actin (ACTC), and sarcoglycan delta (SGCD);

(iii) at least one, two, three or four osteogenic specific genes such as described herein, including for example those selected from the group consisting of: intracellular adhesion molecule 1 (ICAM1), osteomodulin (OMD), tissue inhibitor of metalloporteinase 4 (TIMP4), sex determining region Y box 4 (SOX4), secreted phosphoprotein 1 (SPP1), v-fos FBJ murine osteosarcoma viral oncogene homolog (FOS), alpha V integrin (ITGAV), prolactin (PRL), alpha 4 integrin (ITGA4), peroxisome proliferative activated receptor gamma (PPARG), secreted protein acidic cystein-rich (SPARC) sarcoma amplified sequence (SAS), and bone morphogenetic protein 1 (BMP1), (iii) at least one osteogenic specific gene selected from the group consisting of intracellular adhesion molecule 1 (ICAM1), osteomodulin (OMD), tissue inhibitor of metalloproteinase 4 (TIMP4), sex determining region Y box 4 (SOX4), crystalin alpha B (CRYAB), secreted phosphoprotein 1 (SPP1), v-fos FBJ murine steosarcoma viral oncogene homolog (FOS), alpha V integrin (ITGAV), prolactin (PRL), alpha 4 integrin (ITGA4), peroxisome proliferative activated receptor gamma (PPARG), secreted protein, acidic, cystein-rich (SPARC), sarcoma amplified sequence (SAS), and bone morphogenetic protein 1 (BMP1), or (iv) at least one, two three or four endothelial specific gene such as described herein, including for example those selected from the group consisting of pentaxin-related gene rapidly induced by IL-1 beta (PTX3), selenprotein P plasma 1 (SEPP1), tissue factor pathway inhibitor (TFP1), angiopietin 1 (ANGPT1), angiopoietin-like 2 (ANGPTL2), 3-hydroxy-3-methylglutaryl-Coenzyme A reductase (HMGCR), kruppel-like factor 4 (KLF4), endothelial differentiation lysophosphatidic acid G-protein coupled receptor 2 (EDG2), matrix metalloporiteinase 14 (MPP14), neronal cell adhesion molecule (NRCAM), interleukin 6 (IL6), and tumor necrosis factor, alpha-induced protein 6 (TNFAIP6);

wherein downregulation of said downregulated or universally down-regulated gene as described herein indicates said cell is a de-differentated, pluripotent or multipotent cell, and/or (i) down regulation of expression of the at least one, two, three or four hepatogenic specific gene indicates de-differentiation of a heptogenic specific cell line, (ii) downregulation of expression of the at least one, two, three or four myogenic specific gene indicates de-differentiation of the myogenic specific cell line, (iii) downregulation of expression of the at least one, two, three or four osteogenic specific gene indicates de-differentiation of the osteogenic specific cell line, or (iv) downregulation of expression of the at least one, two, three or four endothelial specific gene indicates de-differentiation of the endothelial specific cell line.

A third aspect of the invention is a combination comprising a plurality of cDNAs (e.g., separately or immobilized on a common substrate such as a microarray) that are differentially expressed in a lineage specific cell line, wherein the plurality of cDNAs consist of cDNAs encoding:

(i) at least one, two, three or four hepatogenic specific genes selected from the group consisting of stearlyl-CoA desaturase (SCD), 3-hydroxy-3-methylglutaryl-Coenzyme A reductase (HMGCR), insulin inducd gene 1 (INSIG1), chromosome 20 open reading frame 97 (C20orf97), lipase A (LIPA), fatty acid desaturase 1 (FADS 1), 7-dehydrocholesterol reductase (DHCR7), apolipoprotein D (APOD), squalene epoxidase (SQLE), cholesterol 25-hydroxylase (CH25H), lipin 1 (LPIN1), insulin induced gene 1 (INSIG1), flavin cntaining monooxygenase 1 (FMO1), aldo-keto reductase family 1 member 1C (AKR1C1), insulin-like growth factor 2 receptor (IGFR2R), ATP-binding cassette sub-family A member 1 (ABCA1), X-box binding protein 1 (XBP1) and mucin 1 (MUC1), or the complements thereof;

(ii) at least one, two, three or four myogenic specific genes selected from the group consisting of insulin-like grwth factor binding protein 3 (IGFBP3), caldesmonin 1 (CALD1), a disintegrin and metallproteinase domain 12 (ADAM12), transglutaminase 2 (TGM2), tumor necrosis factor receptor superfamily member 11b (TNFRSF11B), protein kinase H11 (H11), cardiac muscle alpha actin (ACTC), and sarcoglycan delta (SGCD); at least one osteogenic specific gene selected from the group consisting of: intracellular adhesion molecule 1 (ICAM1), osteomodulin (OMD), tissue inhibitor of metalloporteinase 4 (TIP4), sex determining region Y box 4 (SOX4), secreted phosphoprotein 1 (SPP1), v-fos FBJ murine osteosarcoma viral oncogene homolog (FOS), alpha V integrin (ITGAV), prolactin (PRL), alpha 4 integrin (ITGA4), peroxisome proliferative activated receptor gamma (PPARG), secreted protein acidic cystein-rich (SPARC) sarcoma amplified sequence (SAS), and bone morphogenetic protein 1 (BMP1), or the complements thereof, (iii) at least one, two, three or four osteogenic specific genes selected from the group consisting of: intracellular adhesion molecule 1 (ICAM1), osteomodulin (OMD), tissue inhibitor of metalloporteinase 4 (TIMP4), sex determining region Y box 4 (SOX4), secreted phosphoprotein 1 (SPP1), v-fos FBJ murine osteosarcoma viral oncogene homolog (FOS), alpha V integrin (ITGAV), prolactin (PRL), alpha 4 integrin (ITGA4), peroxisome proliferative activated receptor gamma (PPARG), secreted protein acidic cystein-rich (SPARC) sarcoma amplified sequence (SAS), and bone morphogenetic protein 1 (BMP1), (iii) at least one osteogenic specific gene selected from the group consisting of: intracellular adhesion molecule 1 (ICAM1), osteomodulin (OMD), tissue inhibitor of metalloproteinase 4 (TIMP4), sex determining region Y box 4 (SOX4), crystalin alpha B (CRYAB), secreted phosphoprotein 1 (SPP1), v-fos FBJ murine steosarcoma viral oncogene homolog (FOS), alpha V integrin (ITGAV), prolactin (PRL), alpha 4 integrin (ITGA4), peroxisome proliferative activated receptor gamma (PPARG), secreted protein, acidic, cystein-rich (SPARC), sarcoma amplified sequence (SAS), and bone morphogenetic protein 1 (BMP1), or the complements thereof, or (iv) at least one, two, three or four endothelial specific genes selected from the group consisting of pentaxin-related gene rapidly induced by IL-1 beta (PTX3), selenprotein P plasma 1 (SEPP1), tissue factor pathway inhibitor (TFP1), angiopietin 1 (ANGPT1), angiopoietin-like 2 (ANGPTL2), 3-hydroxy-3-methylglutaryl-Coenzyme A reductase (HMGCR), kruppel-like factor 4 (KLF4), endothelial differentiation lysophosphatidic acid G-protein coupled receptor 2 (EDG2), matrix metalloporiteinase 14 (MPP14), neronal cell adhesion molecule (NRCAM), interleukin 6 (IL6), and tumor necrosis factor, alpha-induced protein 6 (TNFAIP6), or the complements thereof.

BRIEF DESCRIPTION OF THE DRAWINGS

FIG. 1: Methodology for microarray analysis. Microarrays were performed on the Affymetrix HU-133A GeneChip. Data files were analyzed with MAS5 for Present call detections. For differential gene expression, data files were analyzed with dCHIP to identify potential outlying arrays. Data files were then analyzed with Affymetrix LIMMA Graphical User Interface which normalized the raw data files (CEL). LIMMA was used for lineage modeling and statistical determination. Data sets were then analyzed with EASE for gene ontological analyses.

FIG. 2a: Venn diagram comparison of genes present in HAFSC, HESC, and HNSC. Transcriptomes were determined by identifying genes that were present in all 3 triplicates. Comparison of genes present at the specific intersections (A, B, C) represent genes that are present of 2 of the cell types and not the 3rd. There are a greater number of genes common to HESC and HAFSC (A) when compared to the other 2 cell types (B, C).

FIG. 2b: Venn diagram comparison of 3 genetically distinct HAFSC lines and 4 genetically distinct lines. To further address the genetic similarity of HAFSC and HESC, transcriptomes were made from multiple HAFSC lines (H1, J1, A1) and HESC lines (H1, HSF1, HSF6, H9). The transcriptomes are comprised of genes present in all triplicates of each line and further demonstrate the genetic similarity between HAFSC and HESC.

FIG. 3a: Time-points and lineages profiled by microarrays. Microarrays were performed at day 20 and 30 upon myogenic and osteogenic differentiation, day 14 and 30 upon hepatogenic differentiation, and day 30 upon endothelial differentiation.

FIG. 3b: Hierarchical clustering of all microarray data. CEL files were normalized to median chip intensity and analyzed with dCHIP's Model Based Expression Index. A hierarchical cluster was performed on all Present genes and demonstrates each lineage and replicate was appropriately clustered.

DETAILED DESCRIPTION OF THE PREFERRED EMBODIMENTS

"Cells" used in carrying out the present invention are, in general, animal cells, including but not limited to human and non-human cells such as primate (e.g., monkey, chimpanzee, baboon), dog, cat, mouse, rat, horse, cow, pig, rabbit and goat cells, as well as avian, reptile and amphibian cells (e.g., chicken, turkey, duck, geese, quail, pheasant, frog, toad, etc.).

"Stem cell" as used herein refers to a cell that has the ability to replicate through numerous population doublings (e.g., at least 60-80), in some cases essentially indefinitely, and to differentiate into multiple cell types.

"Embryonic stem cell" as used herein refers to a cell that is derived from the inner cell mass of a blastocyst and that is pluripotent.

"Pluripotent" as used herein refers to a cell that has complete differentiation versatility, e.g., the capacity to grow into any of the animals cell types. A pluripotent cell can be self-renewing, and can remain dormant of quiescent with a tissue. Unlike a totipotent cell (e.g., a fertilized, diploid egg cell) a pluripotent cell cannot usually form a new blastocyst."

"Multipotent cell" as used herein refers to a cell that has the capacity to grow into any of a subset of the corresponding animals cell type. Unlike a pluripotent cell, a multipotent cell does not have the capacity to form all of the cell types of the corresponding animal.

"Differential expression" refers to an increased, up-regulated or present, or decreased, down-regulated or absent, gene expression as detected by the absence, presence, or a Bayesian statistic (greater than 0), which corresponds to a significant difference in the amount of transcribed messenger RNA or translated protein in a sample.

The disclosures of all United States patent references cited herein are to be incorporated by reference herein in their entirety.

1. Cells.

Cells that may be used to carry out the present invention are, in general, pluripotent or multipotent cells capable of differentiating into multiple different cell types or lines, including at least one of a hepatogenic-specific (or liver-specific) cell line, a myogenic (or muscle specific) cell line, an osteogenic (or bone specific) cell line, or an endothelial specific cell line. Useful cells for carrying out the invention include but are not limited to embryonic stem cells, parthenogenetic stem cells, amniotic fluid stem cells, and adipose-derived stem cells.

Embryonic stem cells useful for carrying out the present invention are known and described in, for example, U.S. Pat. No. 6,200,806 to Thomson and U.S. Pat. No. 5,843,780 to Thomson.

Adipose-derived stem cells are known and described in, for example, U.S. Pat. No. 6,777,231 to Katz et al. Parthenogenetic stem cells useful for carrying out the present invention are known and described in, for example, J. Hipp et al., *Parthenogenetic Stem Cells*, in Myers, R. A. (Ed.): Meyers Encyclopedia of Molecular Cell Biology and Molecular Medicine, Vol. 10, pp. 71-84 (2d Ed. 2005) and K. Vrana et al., *Non-human Primate Parthenogenetic Stem Cells*, Proc. Natl. Acad. Sci. USA 100 Suppl 1: 11911-6 (2003).

Amniotic fluid stem cells (AFSCs) useful for carrying out the present invention are known and described in, for example, PCT Application WO 03/042405 to Atala and DeCoppi; In't Anker, P. S., et al., *Amniotic fluid as a novel source of mesenchymal stem cells for therapeutic transplantation*. Blood, 2003. 102(4): p. 1548-9; Prusa, A. R., et al., *Oct-4-expressing cells in human amniotic fluid: a new source for stem cell research?* Hum Reprod, 2003. 18(7): p. 1489-93; Kaviani, A., et al., *The amniotic fluid as a source of cells for fetal tissue engineering*. J Pediatr Surg, 2001. 36(11): p. 1662-5; Prusa, A. R. and M. Hengstschlager, *Amniotic fluid* cells and human stem cell research: a new connection. Med Sci Monit, 2002. 8(11): p. RA253-7.

In general, AFSCs are cells, or progeny of cells, that are found in or collected primarily from mammalian amniotic fluid, but may also be collected from mammalian chorionic villus or mammalian placental tissue. The cells are preferably collected during the second trimester of gestation. In mice the cells are most preferably collected during days 11 and 12 of gestation. Preferably the mammalian source is of the same species as the mammalian subject being treated.

In general, the tissue or fluid can be withdrawn by amniocentesis, punch-biopsy, homogenizing the placenta or a portion thereof, or other tissue sampling techniques, in accordance with known techniques. From the sample, stem cells or pluripotent cells may be isolated with the use of a particular marker or selection antibody that specifically binds stem cells, in accordance with known techniques such as affinity binding and/or cell sorting. Particularly suitable is the c-Kit antibody, which specifically binds to the c-kit receptor protein. C-kit antibodies are known (see, e.g., U.S. Pat. Nos. 6,403,559, 6,001,803, and 5,545,533). Particularly preferred is the antibody c-Kit(E-1), a mouse monoclonal IgG that recognizes an epitope corresponding to amino acids 23-322 mapping near the human c-kit N-terminus, available from Santa Cruz Biotechnology, Inc., 2145 Delaware Avenue, Santa Cruz, Calif., USA 95060, under catalog number SC-17806).

AFSCs used to carry out the present invention are pluripotent. Hence, they differentiate, upon appropriate stimulation, into at least osteogenic, adipogenic, myogenic, neurogenic, hematopoitic, and endothelial cells. Appropriate stimulation, for example, may be as follows: Osteogenic induction: The cKit$^+$ cells were cultured in DMEN low glucose with 10% FBS supplementing with 100 nM dexamethasone (Sigma-Aldrich), 10 mM beta-glycerophosphate (Sigma-Aldrich) and 0.05 mM ascorbic acid-2-phosphate (Wako Chemicals, Irving, Tex.); Adipogenic induction: To promote adipogenic differentiation, we cultured c-Kit$^+$, seeded at density of 3000 cells/cm$^2$ in DMEN low glucose medium with 10% FBS supplemented with 1 M dexamethasone, 1 mM 3-isobutyl-1-methylxantine, 10 µg/ml insulin and 60 µM indomethacin (all from Sigma-Aldrich); Myogenic induction: c-Kit$^+$ cells were plated into Matrigel-precoated dish (1 mg/ml, Collaborative Biomedical Products) and cultured in myogenic medium (DMEM low glucose supplemented with 10% horse serum, and 0.5% chick embryo extract from Gibco) followed by treatment of 5-azacytidine (110M, Sigma) added in myogenic medium for 24 h; Endothelial induction: c-Kit$^+$ cells were plated into gelatin-precoated dish and cultured in endothelial basal medium-2 (EBM-2, Clonetics BioWittaker) supplemented with 10% FBS and 1% glutamine (Gibco). In preferred embodiments no feeder layer or leukaemia inhibitory factor (LIF) are required either for expansion or maintenance of AFSCs in the entire culture process.

AFSCs also have substantial proliferative potential. For example, they proliferate through at least 60 or 80 population doublings or more when grown in vitro. In preferred embodiments of AFSCs used to carry out the invention proliferate through 100, 200 or 300 population doublings or more when grown in vitro. In vitro growth conditions for such determinations may be: (a) placing of the amniotic fluid or other crude cell-containing fraction from the mammalian source onto a 24 well Petri dish a culture medium [α-MEM (Gibco) containing 15% ES-FBS, 1% glutamine and 1% Pen/Strept from Gibco supplemented with 18% Chang B and 2% Chang C from Irvine Scientific], upon which the cells are grown to the confluence, (b) dissociating the cells by 0.05% trypsin/EDTA (Gibco), (c) isolating an AFSC subpopulation based on expression of a cell marker c-Kit using mini-MACS (Mitenyl Biotec Inc.), (d) plating of cells onto a Petri dish at a density of 3-8×10$^3$/cm$^2$, and (e) maintaining the cells in culture medium for more than the desired time or number of population doublings.

Preferably, the AFSCs are also characterized by the ability to be grown in vitro without the need for feeder cells (as described in PCT Application WO 03/042405 to Atala and DeCoppi. In preferred embodiments undifferentiated AFSCs stop proliferating when grown to confluence in vivo.

AFSCs used to carry out the present invention are preferably positive for alkaline phosphatase, preferably positive for Thy-1, and preferably positive for Oct. 4, all of which are known markers for embryonic stem cells, and all of which can be detected in accordance with known techniques. See, e.g., Rossant, J., *Stem cells from the Mammalian blastocyst*. Stem Cells, 2001. 19(6): p. 477-82; Prusa, A. R., et al., *Oct-4-expressing cells in human amniotic fluid: a new source for stem cell research*? Hum Reprod, 2003. 18(7): p. 1489-93.

In a particularly preferred embodiment, the AFSCs do not form a teratoma when undiferentiated AFSCs are grown in vivo. For example, undifferentiated AFSCs do not form a teratoma within one or two months after intraarterial injection into a 6-8 week old mouse at a dose of 5×10$^6$ cells per mouse.

2. Differentiation and De-Differentiation of Cells.

Differentiation of cells can be carried out in a variety of ways which are known to those skilled in the art or will be apparent based on the disclosure herein. For example, to induce differentiation in monolayer cultures, cells are cultured for 2 weeks without passage onto a fresh feeder layer. To induce differentiation in suspension culture, the cells are passed onto a gelatinized plate to eliminate possible contamination by fibroblasts. After. 4 to 7 days in culture, colonies are gently dislodged from the plate and disaggregated after incubation in 0.25% trypsin-EDTA for 10-15 min. Dissociated cells are cultured in a microdrop of EG culture medium containing 0.3 uM retmoic acid on a 35-mm nonadhesive petridish. Suspension cultures are monitored daily for embrygid body formation which is indicative of a differentiated phenotype. Cell culture media is changed every other day. A broadly applicable method of obtaining pure populations of specific cell types or lineages during cell differentiation involves the use of a cell-type specific promoter driving a selectable marker gene (e.g., one providing resistance to an otherwise toxic drug). Under the appropriate differentiation conditions, in the presence of the drug, only those cells that can activate the selectable marker (those undergoing the desired differentiation) survive. See, e.g., U.S. Pat. No. 6,562,619.

In still another example, the cells may be grown in a reprogramming media to induce differentiation to a particular cell type or line, such as described in US Patent Application 2003/0046722A1 to Collas.

For de-differentiation, a somatic cell is manipulated genetically and/or using growth factors/extracellular matrices identified from microarrays. For example, one can transfect one or two genes into a somatic cell like a fibroblast, and culture the cells with the growth factors and extracellular matrix components identified from the microarray data, to make an an embryonic like stem cell, or to make a proliferating progenitor cell.

3. cDNAs and Their Uses.

cDNAs can be prepared by a variety of synthetic or enzymatic methods well known in the art. cDNAs can be synthesized, in whole or in part, using chemical methods well known in the art (Caruthers et al. (1980) Nucleic Acids Symp.

Ser. (7)215-233). Alternatively, cDNAs can be produced enzymatically or recombinantly, by in vitro or in vivo transcription. See, e.g., U.S. Pat. No. 6,544,742 (Incyte).

Nucleotide analogs can be incorporated into cDNAs by methods well known in the art. The only requirement is that the incorporated analog must base pair with native purines or pyrimidines. For example, 2,6-diaminopurine can substitute for adenine and form stronger bonds with thymidine than those between adenine and thymidine. A weaker pair is formed when hypoxanthine is substituted for guanine and base pairs with cytosine. Additionally, cDNAs can include nucleotides that have been derivatized chemically or enzymatically.

cDNAs can be synthesized on a substrate. Synthesis on the surface of a substrate may be accomplished using a chemical coupling procedure and a piezoelectric printing apparatus as described by Baldeschweiler et al. (PCT publication WO95/251116). Alternatively, the cDNAs can be synthesized on a substrate surface using a self-addressable electronic device that controls when reagents are added as described by Heller et al. (U.S. Pat. No. 5,605,662). cDNAs can be synthesized directly on a substrate by sequentially dispensing reagents for their synthesis on the substrate surface or by dispensing preformed DNA fragments to the substrate surface. Typical dispensers include a micropipette delivering solution to the substrate with a robotic system to control the position of the micropipette with respect to the substrate. There can be a multiplicity of dispensers so that reagents can be delivered to the reaction regions efficiently.

cDNAs can be immobilized on a substrate by covalent means such as by chemical bonding procedures or UV irradiation. In one method, a cDNA is bound to a glass surface which has been modified to contain epoxide or aldehyde groups. In another method, a cDNA is placed on a polylysine coated surface and UV cross-linked to it as described by Shalon et al. (WO95/35505). In yet another method, a cDNA is actively transported from a solution to a given position on a substrate by electrical means. cDNAs do not have to be directly bound to the substrate, but rather can be bound to the substrate through a linker group. The linker groups are typically about 6 to 50 atoms long to provide exposure of the attached cDNA. Preferred linker groups include ethylene glycol oligomers, diamines, diacids and the like. Reactive groups on the substrate surface react with a terminal group of the linker to bind the linker to the substrate. The other terminus of the linker is then bound to the cDNA. Alternatively, polynucleotides, plasmids or cells can be arranged on a filter. In the latter case, cells are lysed, proteins and cellular components degraded, and the DNA is coupled to the filter by UV cross-linking.

A cDNA may represent the complete coding region of an mRNA or be designed or derived from unique regions of the mRNA or genomic molecule, an intron, a 3' untranslated region, or from a conserved motif. The cDNA is at least 18 contiguous nucleotides in length and is usually single stranded. Such a cDNA may be used under hybridization conditions that allow binding only to an identical sequence, a naturally occurring molecule encoding the same protein, or an allelic variant. Discovery of related human and mammalian sequences may also be accomplished using a pool of degenerate cDNAs and appropriate hybridization conditions. Generally, a cDNA for use in Southern or northern hybridizations may be from about 400 to about 6000 nucleotides long. Such cDNAs have high binding specificity in solution-based or substrate-based hybridizations. An oligonucleotide, a fragment of the cDNA, may be used to detect a polynucleotide in a sample using PCR.

The cDNAs of the invention can be incorporated, as lineage-specific groups thereof, into kits for the detection of lineage-specific differentiation, or de-differentiation, as described in U.S. Pat. No. 6,489,455 to Chenchik et al. (Clontech) and U.S. Pat. No. 5,994,076 to Chenchik et al. (Clontech).

4. Detection of Lineage-Specific Gene Expression.

Detection of the differential expression (including upregulation and downregulation of expression) of a gene or nucleic acid is known and can be carried out in accordance with known techniques (e.g., utilizing cDNAs as described herein), or variations thereof that will be apparent to persons skilled in the art in light of the instant disclosure. See, e.g., U.S. Pat. Nos. 6,727,006; 6,682,888; 6,673,549; 6,673,545; 6,500,642; 6,489,455.

For example, the combinations of the invention may be used on an array. When the cDNAs of the invention are employed on a microarray, the cDNAs are arranged in an ordered fashion so that each cDNA is present at a specified location. Because the cDNAs are at specified locations on the substrate, the hybridization patterns and intensities, which together create a unique expression profile, can be interpreted in terms of expression levels of particular genes and can be correlated with or used to identify differentiation and/or de-differentiation as described herein.

The cDNAs or fragments or complements thereof may be used in various hybridization technologies, e.g., to detect differential expression of genes as described herein in cells as described herein. The cDNAs may be labeled using a variety of reporter molecules by either PCR, recombinant, or enzymatic techniques. For example, a commercially available vector containing the cDNA is transcribed in the presence of an appropriate polymerase, such as T7 or SP6 polymerase, and at least one labeled nucleotide. Commercial kits are available for labeling and cleanup of such cDNAs. Radioactive (Amersham Pharmacia Biotech (APB), Piscataway N.J.), fluorescent (Operon Technologies, Alameda Calif.), and chemiluminescent labeling (Promega, Madison Wis.) are well known in the art.

The stringency of hybridization is determined by G+C content of the cDNA, salt concentration, and temperature. In particular, stringency is increased by reducing the concentration of salt or raising the hybridization temperature. In solutions used for some membrane based hybridizations, addition of an organic solvent such as formamide allows the reaction to occur at a lower temperature. Hybridization may be performed with buffers, such as 5× saline sodium citrate (SSC) with 1% sodium dodecyl sulfate (SDS) at 60° C., that permit the formation of a hybridization complex between nucleic acid sequences that contain some mismatches. Subsequent washes are performed with buffers such as 0.2×SSC with 0.1% SDS at either 45° C. (medium stringency) or 65-68° C. (high stringency). At high stringency, hybridization complexes will remain stable only where the nucleic acid molecules are completely complementary. In some membrane-based hybridizations, preferably 35% or most preferably 50%, formamide may be added to the hybridization solution to reduce the temperature at which hybridization is performed. Background signals may be reduced by the use of detergents such as Sarkosyl or Triton X-100 (Sigma Aldrich, St. Louis Mo.) and a blocking agent such as denatured salmon sperm DNA. Selection of components and conditions for hybridization are well known to those skilled in the art and are reviewed in Ausubel et al. (1997, Short Protocols in Molecular Biology, John Wiley & Sons, New York N.Y., Units 2.8-2.11, 3.18-3.19 and 4-64.9).

Applications of the methods and techniques described herein include, but are not limited to: optimizing conditions for stem cell differentiation (e.g., for therapy); evaluating stem cell differentiation; defining lineage-specific genetic signatures; defining "stemness" (the genetic character of a stem cell) signature; characterizing stem cells from different sources; evaluating tissue function; evaluating diseased tissue function; evaluating engineered tissue function; and evaluating stem cell potential for cell therapy.

The present example is explained in greater detail in the following non-limiting Examples.

Experimental

HAFSC represent a novel immunocompatible stem cell resource in that they are pluripotential like HESC, but like adult stem cells, do not form teratomas when injected in vivo. They have the expansion potential of HESC, but are as simple to grow as adult stem cells. We have previously shown that we can differentiate HAFSC in vitro into multiple lineages and have done extensive characterization with RT-PCR, western blots, immunocytochemistry and in vivo studies on their differentiation derivatives. Microarrays allow one to measure the expression levels of thousands of known and unknown genes, and have been primarily used to identify enriched genes in undifferentiated stem cells [5-8]. Here we use microarrays to understand the global genetic mechanisms involved in their multilineage differentiation. We began our analysis by first identifying the genetic components of HAFSC with comparison to other types of stem cells such as; pluripotential stem cells (HESC) and mulitpotent adult stem cells (HNSC) [9]. We then identified the genetic changes upon their differentiation into a particular lineages such as bone, muscle, endothelia, liver and then identified the genetic mechanisms common to all lineages. By dissecting away those genes we identified as being up-regulated in all lineages from those we identified as being up-regulated in a particular lineage, we were able to identify a set of lineage specific targets. Of the genes most significantly up-regulated upon differentiation amongst all lineages are genes involved in extracellular matrix (ECM) production. These genes, which are up-regulated by 20-80 fold, are also significantly up-regulated upon human embryonic stem cell and monkey parthenogenetic stem cell differentiation and signify the potential importance of scaffold design for stem cell differentiation.

Methods:

Differentiation Protocol:

Human amniotic fluid was collected from 14-18 week old fetuses and grown in basic media with serum. A progenitor cell was isolated and expanded. Here we used three genetically distinct lines, the A1 and H1 are two genetically distinct lines created from two different amniotic fluid samples and differ in passage numbers, 33 and 7; while the J1 line was created by pooling five different amniotic fluid samples, passage 7. HAFSC were differentiated as follows:

Endothelial: AFSC were cultured in endothelial basal medium on gelatin coated dishes. Full differentiation is detected within 30 days in culture, and demonstration of capillary formation upon culturing on matrigel.

Hepatocytes: AFSC were grown on matrigel for the first 14 days, then reseeded onto collagen. Growth factor supplements include HGF, Insulin, oncostatin M, dexamethasone, fibroblast growth factor 4, and monothioglycerol. The cells show positive staining for albumin at day 45 post differentiation and also express the transcription factor HNF4α, the c-met receptor, the MDR membrane transporter, albumin, and α-fetoprotein.

Muscle: AFSC were grown on matrigel with media supplemented with horse serum and chick embryo extract. Five-azacytidine was supplemented for the first 24 Morphological changes and the detection of Myf6 and MyoD occur around day 8, and their repression at day 16.

Bone: AFSC were grown in media supplemented with dexamethasone, beta-glycerophosphate, and ascorbic acid-2-phosphate. Phenotypic changes occur within 4 days, and at 16 days, show a typical lamellar bone-like structures with calcium deposition. Von Kossa staining was positive at Day 30.

Microarrays were performed on the undifferentiated AFSC lines H1, J1, and A1 at 20 and 30 days following myogenic and osteogenic differentiation, 14 and 30 days following hepatogenic differentiation, and 30 days following vasculogenic differentiation. RNA was isolated using RNAseB and hybridized to the Affymetrix U133A GeneChip (Affymetrix, Santa Clara, Calif.) as described by the Affymetrix protocol.

Our analysis consisted of using a variety of computer programs (FIG. 1). Data files were first analayzed with Microarray Suite 5.0 for Present/Absent detection calls. For a gene to be Present in each "transcriptome," it was identified as being Present ($p<0.04$) in all 3 biological replicates.

Raw data files were incorporated into dCHIP, normalized to median chip intensity, and model based expression index was computed on Perfect Match/Miss signal intensities [10]. Probe-level data was then summarized with RMA [11], and differentially expressed genes were found with LIMMA [12] using the graphical user interface provided by affylmGUI, the sister package of limmaGUI [13]. Differentially expressed genes were ranked using the B statistic [12] [14] and P values were adjusted using the FDR method of Benjamini and Hochberg [15]. Genes that had a B value of greater than 1 (Log of Odds score), with a False Discovery Rate modified p value of less than 0.003 were selected as being differentially expressed. To identify the genetic themes present in the data sets, the probe sets were loaded into the EASE [16] and then clustered based on their Gene Ontologies (GO Bio, GO Molecular Function, and Go Cellular Component) and for annotation. A fisher exact probability test was used to identify those statistically over-represented pathways.

Results

The transcriptional components of HAFSC, HESC, and HNSC. Stemness, the ability to self-renew and differentiate, differs amongst pluripotential and multipotential stem cells. The former has the capability of differentiating into all cell types of the embryo while the later are capable of differentiating into only a few tissues. HESC are the best characterized pluripotential stem cells, and HNSC represent a well established multipotential stem cell. Since previous in vitro and in vivo studies have indicated that HAFSC represent a unique stage amongst the differentiation spectrum, we sought a genetic explanation for this.

As a way to understand the relationship between HAFSC and other stem cells, we created transcriptomes from HAFSC and compared it to an established pluripotential transcriptome (HESC) and a multipotential transcriptome (HNSC).

Affymetrix U133A microarrays were performed on HAFSC (A1 line passage 33) and its transcriptional signature was compared to the publicly available data files of the H1 HESC line [8] and HNSC [9]. There were 6024 probe sets common to all 3 human stem cell types (FIG. 2a). This data set was then clustered based on their GO BIO ontologies and the predominating genetic themes of this data set are metabolism, RNA metabolism, RNA processing, intracellular transport, RNA splicing and protein metabolism.

As a way to quantify the genetic similarity of HAFSC, HNSC and HESC we then compared the number of genes present in 2 of the cell types and not the other (Present in HESC-HAFSC and not HNSC (A), Present in HESC-HNSC and not AFSC (B), Present in HAFSC-HNSC and not HESC (C) (FIG. 2a). We identify 3.3 times as many genes in common between HESC and AFSC when compared to HNSC (A/B) and 3.2 times as many genes in common between AFSC and HESC when compared to HNSC (A/C); while NSC have approximately as many genes in common with both HAFSC and HESC (461 and 458 genes). Upon the spectrum of differentiation, this data suggests that AFSC represent a unique stage of development whose transcriptional signature is much more similar to HESC than HNSC.

To further address the transcriptional similarities between HAFSC and HESC, we began by addressing the issue of genetic variability between cell lines by creating a "core HAFSC transcriptome" comprised of genes present in all 3 biological replicates of 3 genetically distinct lines and a "core HESC transcriptome" comprised of genes Present in all triplicates of 4 different HESC lines (H1, HSF1, HSF6, H9). We then compared the HAFSC and HESC transcriptomes and identified 4548 genes which were detected as Present (p<0.04) in all 7 lines (FIG. 2b). We then clustered this data set based on their GO BIO ontology and identify pathways involved in autocrine/paracrine growth/differentiation signaling, receptors, extracellular matrices (ECM) and signal transduction genes that are conserved between HAFSC and HESC. Taken together, by comparing and contrasting the different transcriptional components we created a pluripotential signature (genes present in HAFSC and HESC and not in HNSC) and a multipotential signature (genes present in HAFSC, NSC and HESC). Furthermore, this data demonstrates that even though HAFSC and HESC are distinct cell types with potential differences in their developmental stages, they share a relatively common transcriptional signature.

Microarray analysis of HAFSC multi-lineage differentiation. In order to understand the genetic mechanisms involved in HAFSC multilineage differentiation, microarrays were performed at multiple time points along their differentiation into liver, bone, muscle, and endothelia (FIG. 3a). Microarray analysis was performed on day 20 and day 30 for muscle and bone differentiation because it is at day 20 when they express tissue specific markers, and day 30 for endothelia because that is when they are capable of forming capillaries. We chose day 30 for hepatocytes because we have previously identified hepatocyte markers at day 30, and day 14 for hepatocytes because we wanted to understand the early commitments of liver differentiation.

For an unbiased assessment of our raw data, we analyzed the CEL files with dCHIP. We first normalized all chips to the median chip intensity, ran the model based expression index to identify probe outliers using and then performed a hierarchical cluster on all Present genes (FIG. 3b). All data files were clustered according to their replicate, time point, and lineage, as expected. The only exception was the Hepato-d14 (Hepatocyte, day 14) data set whose transcriptional profile was identified as more similar to the osteogenic lineage.

Probe-level data was summarized with RMA [11] to remove probe level noise distributed amongst all CEL files and differentially expressed genes were identified with LIMMA [12]. Genes were selected as being differentially expressed using a Bayesian statistic value greater than 1 (the B value is the likelihood of odds score) and a False Discovery Rate modified P value (<0.003) for differential gene expression. Using these stringent criteria, we identified genes that were up and down-regulated upon differentiation into bone, muscle, endothelia, and liver at 14, 20 and 30 days of differentiation (Table 1).

TABLE 1

Number of genes identified upon differentiation.[1]

|  | Down | Up | Lineage Specific Up |
| --- | --- | --- | --- |
| Hepatogenesis d30 | 530 | 317 | 110 |
| Hepatogenesis d14 | 466 | 143 | 33 |
| Osteogenesis d30 | 587 | 299 | 91 |
| Osteogenesis d20 | 357 | 161 | 20 |
| Vasculogenesis d30 | 611 | 303 | 124 |
| Myogenesis d30 | 524 | 168 | 61 |
| Myogenesis d20 | 1018 | 287 | 120 |

[1]Genes were identified as being up and down-regulated for each lineage. "Lineage specific" genes were identified by subtracting those genes that were up-regulated from the "universally" up-regulated genes.

A "universally" conserved signature upon HAFSC differentiation. We sought to distinguish between the genetic mechanisms that are common to all 4 lineages ("universal") and those specific to each lineage ("lineage specific"). To identify the "universal" signature of genes, we combined all day 30 data sets a treated them as a single data point, and compared it to the undifferentiated. We identified a signature of 1017 genes as being "universally" down-regulated and 379 genes as being "universally" up-regulated amongst all lineages. Those transcripts that increased "universally" represent differentiation genes and those that decreased "universally" in all lineages represent a data set of potential HAFSC derived "stemness" genes.

We then clustered the "universally" up-regulated genes using different ontologies, GO BIO and GO Molecular Function. The most over-represented GO BIO themes were antigen presentation (validating previous reports that Amniotic Fluid derived stem cells are immunoprivileged), negative regulation of the cell cycle, and the Jak-Stat pathway, cell cycle, epigenetics, and transcription. The most over-represented GO Molecular Function was MHC Class I receptor activity and extracellular matrix structural constituents.

Of the 1017 "universally" down-regulated genes, we identified 813 present in H1-HESC, 771 in H9-HESC, 636 in HSF1-HESC, 720 in HSF6-HESC, while 407 were present in skeletal muscle (this data set was comprised of genes present in 8 of 8 Affymetrix U133A data files), and 372 genes present in diaphragmatic muscle. We then created a new signature of 607 genes that were "universally" down-regulated and present in all 4 HESC lines (H1, H9, HSF1, HSF6). As expected, the majorities of genes in the AFSC derived "stemness" signature are present in the HESC transcriptome, and represent a novel set of stemness targets.

Lineage Specific Differentiation Signatures. We wanted to identify a signature of genes that were up-regulated in a lineage specific manner. By subtracting out the "universally" up-regulated genes from those identified as being up-regulated in each lineage, we created a lineage specific signature (Table 1). Using this method we identify 69 Osteo-d30, 29 Hepato-d14, 83 Hepato-d30, 93 Endo-d30, and 143 Myo-d20-30.

We clustered these data sets using different gene ontology classifications. The liver specific signature of genes was clustered based on their GO BIO ontology, GO Molecular Function and Swiss Prot Ontologies and we identified numerous processes involved in hepatocyte specific functions such as sterol, lipid, cholesterol metabolism and biosynthesis (Table 2a). Table 2b shows the top 15 genes that are up-regulated in our lineage specific data set, all of which play a crucial role in liver function, followed by their False Discovery Rate (FDR) modified p-value, B value (Log Odds ratio) and fold change.

This type of analysis was also performed for the myogenic lineage showing the predominant theme of this data set were genes involved in muscle development and adhesion (Table 3a). Table 3b represents some of the most statistically significant and biologically relevant genes known to be involved in myogenesis such as CALD1, SGCD, ADAM12 and GATA6.

TABLE 2a

Gene Ontology analysis of "lineage specific" genes up-regulated upon hepatogenic differentiation.[1]

| Gene Category | List Hits | EASE score |
|---|---|---|
| sterol metabolism* | 15 | 1.65E−11 |
| cholesterol metabolism* | 14 | 7.65E−11 |
| sterol biosynthesis* | 11 | 1.10E−10 |
| Cholesterol biosynthesis*** | 9 | 2.80E−10 |
| cholesterol biosynthesis* | 10 | 3.72E−10 |
| steroid biosynthesis* | 13 | 3.93E−09 |
| steroid metabolism* | 16 | 2.33E−08 |
| lipid metabolism* | 31 | 1.06E−07 |
| oxidoreductase activity** | 32 | 1.17E−07 |
| alcohol metabolism* | 19 | 9.86E−07 |
| lipid biosynthesis* | 16 | 1.69E−06 |
| NADP*** | 11 | 1.71E−05 |
| Oxidoreductase*** | 23 | 2.88E−05 |
| Extracellular matrix*** | 13 | 3.49E−05 |
| Glycoprotein*** | 72 | 4.70E−05 |
| physiological process* | 207 | 5.84E−05 |
| extracellular matrix structural constituent** | 10 | 7.18E−05 |
| Sterol biosynthesis*** | 4 | 4.61E−04 |
| isoprenoid biosynthesis* | 4 | 6.67E−04 |
| biosynthesis* | 37 | 8.72E−04 |
| Polymorphism*** | 54 | 1.15E−03 |
| trans-1\,2-dihydrobenzene-1\,2-diol dehydrogenase activity** | 3 | 1.22E−03 |

[1]Genes were clustered based on their Gene Ontology Bio*, Gene Ontology Molecular Function, and Swissprot Ontology* using EASE TABLE 3a Gene Ontology analysis of "lineage specific" genes up-regulated upon myogenic differentiation.

| Gene Category | List Hits | EASE score |
|---|---|---|
| Signal*** | 27 | 1.77E−05 |
| Glycoprotein*** | 26 | 4.74E−04 |
| muscle development* | 6 | 2.86E−03 |
| protein modification* | 16 | 3.39E−03 |
| insulin-like growth factor binding** | 3 | 7.51E−03 |
| acyltransferase activity** | 5 | 9.39E−03 |
| transferase activity\, transferring groups other than amino-acyl groups** | 5 | 9.97E−03 |
| cell-matrix adhesion* | 4 | 1.24E−02 |
| transferase activity\, transferring acyl groups** | 5 | 1.29E−02 |
| cell adhesion* | 10 | 1.71E−02 |
| ER to Golgi transport* | 3 | 1.77E−02 |
| glycosaminoglycan binding** | 4 | 2.21E−02 |
| phosphatidylcholine-sterol O-acyltransferase activity** | 3 | 2.55E−02 |
| extracellular matrix structural constituent** | 4 | 2.66E−02 |
| cell adhesion molecule activity** | 7 | 3.37E−02 |
| growth factor binding** | 3 | 3.61E−02 |
| Heparin-binding*** | 3 | 4.24E−02 |
| protein metabolism* | 24 | 4.38E−02 |
| EGF-like domain*** | 4 | 4.50E−02 |
| O-acyltransferase activity** | 3 | 4.99E−02 |

TABLE 2b

List of "hepatogenic specific" genes identified upon differentiation.

| Name | Symbol | PValue | B | fc |
|---|---|---|---|---|
| stearoyl-CoA desaturase (delta-9-desaturase) | SCD | 0.000748 | 2.386358 | 26.72281 |
| 3-hydroxy-3-methylglutaryl-Coenzyme A reductase | HMGCR | 0.000156 | 4.518047 | 18.63574 |
| insulin induced gene 1 | INSIG1 | 1.91E−05 | 7.4004 | 17.5087 |
| chromosome 20 open reading frame 97 | C20orf97 | 6.23E−06 | 8.9504 | 16.91229 |
| lipase A, lysosomal acid, cholesterol esterase (Wolman disease) | LIPA | 2.79E−06 | 9.966624 | 12.38052 |
| fatty acid desaturase 1 | FADS1 | 5.22E−07 | 12.27617 | 11.71269 |
| 7-dehydrocholesterol reductase | DHCR7 | 9.23E−05 | 5.241665 | 11.31371 |
| apolipoprotein D | APOD | 0.000262 | 3.795505 | 10.26741 |
| squalene epoxidase | SQLE | 0.000231 | 3.971017 | 9.849155 |
| cholesterol 25-hydroxylase | CH25H | 1.86E−07 | 13.91938 | 9.713559 |
| lipin 1 | LPIN1 | 7.56E−06 | 8.664026 | 9.646463 |
| insulin induced gene 1 | INSIG1 | 0.000649 | 2.5955 | 6.634556 |
| flavin containing monooxygenase 1 | FMO1 | 4.26E−05 | 6.305874 | 4.531536 |
| aldo-keto reductase family 1, member C1 (dihydrodiol dehydrogenase 1, 20-alpha (3-alpha)-hydroxysteroid dehydrogenase) | AKR1C1 | 0.000199 | 4.190194 | 4.40762 |
| insulin-like growth factor 2 receptor | IGF2R | 0.000206 | 4.133336 | 4.169863 |
| ATP-binding cassette, sub-family A (ABC1), member 1 | ABCA1 | 0.000107 | 5.055351 | 3.24901 |
| X-box binding protein 1 | XBP1 | 0.00021 | 4.109397 | 2.445281 |
| mucin 1, transmembrane | MUC1 | 0.000308 | 3.599832 | 2.143547 |

TABLE 3b

List of "myogenic specific" genes identified upon differentiation.

| Gene Name | Gene Symbol | PValue | B | fc |
|---|---|---|---|---|
| insulin-like growth factor binding protein 3 | IGFBP3 | 0.000156 | 4.849089 | 14.3204 |
| caldesmon 1 | CALD1 | 0.000349 | 3.76869 | 13.26911 |
| a disintegrin and metalloproteinase domain 12 (meltrin alpha) | ADAM12 | 1.77E–06 | 10.54941 | 10.26741 |
| transglutaminase 2 (C polypeptide, protein-glutamine-gamma-glutamyltransferase) | TGM2 | 4.33E–06 | 9.406555 | 5.735821 |
| tumor necrosis factor receptor superfamily member 11b (osteoprotegerin) | TNFRSF11B | 0.00162 | 1.701486 | 2.378414 |
| protein kinase H11 | H11 | 0.000586 | 3.069655 | 1.786332 |
| actin, alpha, cardiac muscle | ACTC | 0.00271 | 1.001418 | 1.557249 |
| sarcoglycan, delta (35 kDa dystrophin-associated glycoprotein) | SGCD | 0.00138 | 1.914714 | 1.395711 |

In Table 4a, we clustered the osteo-specific genes using gene ontology. The predominant theme in this data set were ECM (Collagen14A1, MAGP2, DPT, Table 4b), as one would expect considering the predominant function of bone is for physical strength and support.

TABLE 4a

Gene Ontology analysis of "lineage specific" genes up-regulated upon osteogenic differentiation.

| Gene Category | List Hits | EASE score |
|---|---|---|
| Signal*** | 72 | 6.98E–11 |
| Extracellular matrix*** | 18 | 2.85E–10 |
| Glycoprotein*** | 76 | 4.04E–10 |
| Interferon induction*** | 11 | 5.92E–10 |
| extracellular matrix structural constituent** | 14 | 5.44E–09 |
| morphogenesis* | 41 | 1.17E–06 |
| response to biotic stimulus* | 36 | 1.17E–06 |
| cell adhesion* | 28 | 1.29E–06 |
| immune response* | 32 | 1.39E–06 |
| organogenesis* | 37 | 3.64E–06 |
| defense response* | 32 | 1.15E–05 |
| response to external stimulus* | 44 | 2.14E–05 |
| development* | 53 | 3.56E–05 |
| Connective tissue*** | 7 | 3.87E–05 |
| cell communication* | 74 | 1.69E–04 |
| structural molecule activity** | 26 | 7.33E–04 |
| Basement membrane*** | 5 | 7.67E–04 |
| EGF-like domain*** | 9 | 2.25E–03 |
| cell adhesion molecule activity** | 15 | 2.67E–03 |
| Collagen*** | 6 | 2.82E–03 |
| receptor activity** | 37 | 3.30E–03 |
| Hydroxylation*** | 6 | 3.69E–03 |

TABLE 4b

List of "osteogenic specific" genes identified upon differentiation.

| Name | Symbol | PValue | B | fc |
|---|---|---|---|---|
| intercellular adhesion molecule 1 (CD54), human rhinovirus receptor | ICAM1 | 0.0015 | 1.29941 | 6.32033 |
| osteomodulin | OMD | 1.64E–05 | 7.23681 | 5.979397 |
| tissue inhibitor of metalloproteinase 4 | TIMP4 | 3.13E–06 | 9.44493 | 4.924578 |
| SRY (sex determining region Y)-box 4 | SOX4 | 0.000196 | 3.99424 | 4.890561 |
| crystallin, alpha B | CRYAB | 0.000165 | 4.23785 | 4.789915 |
| secreted phosphoprotein 1 (osteopontin, bone sialoprotein I, early T-lymphocyte activation 1) | SPP1 | 0.00122 | 1.57094 | 4.658934 |
| v-fos FBJ murine osteosarcoma viral oncogene homolog | FOS | 0.00117 | 1.64253 | 3.863745 |
| integrin, alpha V (vitronectin receptor, alpha polypeptide, antigen CD51) | ITGAV | 0.000594 | 2.54871 | 3.630077 |
| prolactin | PRL | 1.14E–05 | 7.71067 | 3.458149 |
| integrin, alpha 4 (antigen CD49D, alpha 4 subunit of VLA-4 receptor) | ITGA4 | 0.000349 | 3.25342 | 3.031433 |
| peroxisome proliferative activated receptor, gamma | PPARG | 0.000997 | 1.86923 | 2.496661 |
| secreted protein, acidic, cysteine-rich (osteonectin) | SPARC | 0.00016 | 4.28132 | 2.462289 |
| sarcoma amplified sequence | SAS | 0.000624 | 2.48282 | 2 |
| bone morphogenetic protein 1 | BMP1 | 0.00168 | 1.13847 | 1.65749 |

Lastly, we clustered the endothelial lineage specific targets and the predominant gene ontological themes were those involving extracellular matrix (Table 5a) as one would expect, considering their predominant function is a physical conduit of fluid. Table 5b represents some of the endothelia specific targets we identified such as angiopoietin 1, endothelial differentiation, lysophosphatidic acid G-protein-coupled receptor, 2 and Kruppel-like factor 4. Taken together, the specific signatures we identified from different lineages demonstrate our ability to identify tissue specific mechanisms of differentiation TABLE 5a Gene Ontology analysis of "lineage specific" genes up-regulated upon endothelial differentiation.

| Gene Category | List Hits | EASE score |
|---|---|---|
| sterol metabolism* | 11 | 2.21E−07 |
| Cholesterol biosynthesis*** | 7 | 2.51E−07 |
| lipid metabolism* | 29 | 2.85E−07 |
| sterol biosynthesis* | 8 | 7.56E−07 |
| cholesterol metabolism* | 10 | 1.08E−06 |
| steroid metabolism* | 13 | 3.29E−06 |
| cholesterol biosynthesis* | 7 | 3.69E−06 |
| lipid biosynthesis* | 14 | 1.91E−05 |
| steroid biosynthesis* | 9 | 2.32E−05 |
| oxidoreductase activity** | 24 | 1.87E−04 |
| NADP*** | 9 | 2.71E−04 |
| alcohol metabolism* | 14 | 4.35E−04 |
| response to external stimulus* | 42 | 5.30E−04 |
| trans-1\,2-dihydrobenzene−1\,2-diol dehydrogenase activity** | 3 | 1.05E−03 |
| Oxidoreductase*** | 18 | 1.26E−03 |
| regulation of biological process* | 16 | 1.73E−03 |
| cell differentiation* | 11 | 1.83E−03 |
| response to biotic stimulus* | 29 | 2.22E−03 |
| physiological process* | 189 | 2.53E−03 |
| Isoprene biosynthesis*** | 3 | 2.74E−03 |
| immune response* | 25 | 3.10E−03 |
| regulation of cell proliferation* | 13 | 3.23E−03 |

We first created a transcriptional parts list of pluripotential and multipotential stem cells. Although there are over 7386 transcripts present in the HAFSC transcriptome, we began to prioritize these targets by looking for commonalities between other multipotential stem cells such as HNSC, and pluripotential stem cells such as HESC (identifying over 4548 transcripts in common between 3 genetic unique cell lines of HAFSC and 4 of HESC). The intersection of all three cell types, HESC, HAFSC, and HNSC represent a combined set of potential housekeeping and/or multipotential "stemness" genes. We are particular interested in those genes that were only Present in HESC and HAFSC (1496 transcripts) because they might represent new pluripotential markers, while the other data set intersections probably contain new stem cell markers and their understanding will help discriminate between pluripotency and multipotency.

We identified a signature of genes that are down regulated amongst all lineages. These down-regulated or "stemness" genes are enriched in the undifferentiated state and could be responsible for self-renewal and pluripotentiality. We then prioritized this genetic signature by comparing it to genes that are Present in different HESC lines. It is interesting to note that some of these genes are present in more HESC lines than others, and this might begin to explain why some HESC lines grow and differentiate better than others (unreported observations).

There are signatures of genes that are up regulated amongst all lineages. These up-regulated genes or "differentiation" genes could be responsible for exiting the "stemness" state. Targeting these "universally" up-regulated genes might improve the speed and quality of differentiation. Furthermore, these genes might serve as "brakes" which prevent adult cells from de-differentiating and might serve as reprogramming targets.

A predominating theme of the "universally" up-regulated data set includes a number of genes involved in ECM production. It has been known that matrices can induce differentiation into a particular lineage but this data demonstrates that TABLE 5b List of "endothelial specific" genes identified upon differentiation.

| Name | Symbol | PValue | B | fc |
|---|---|---|---|---|
| pentaxin-related gene, rapidly induced by IL-1 beta | PTX3 | 7.49E−07 | 11.73222 | 33.12848 |
| selenoprotein P, plasma, 1 | SEPP1 | 2.08E−07 | 13.45948 | 23.26356 |
| tissue factor pathway inhibitor (lipoprotein-associated coagulation inhibitor) | TFPI | 7.71E−05 | 5.351259 | 8.938297 |
| angiopoietin 1 | ANGPT1 | 5.97E−05 | 5.677872 | 7.568461 |
| angiopoietin-like 2 | ANGPTL2 | 9.72E−07 | 11.32051 | 6.634556 |
| 3-hydroxy-3-methylglutaryl-Coenzyme A reductase | HMGCR | 0.000391 | 3.192566 | 6.32033 |
| Kruppel-like factor 4 (gut) | KLF4 | 2.88E−05 | 6.631168 | 5.61778 |
| endothelial differentiation, lysophosphatidic acid G-protein-coupled receptor, 2 | EDG2 | 0.000684 | 2.464807 | 3.458149 |
| matrix metalloproteinase 14 (membrane-inserted) | MMP14 | 0.000719 | 2.401224 | 2.732081 |
| neuronal cell adhesion molecule | NRCAM | 0.00157 | 1.342647 | 2.514027 |
| interleukin 6 (interferon, beta 2) | IL6 | 0.000859 | 2.14531 | 1.781386 |
| tumor necrosis factor, alpha-induced protein 6 | TNFAIP6 | 0.000742 | 2.341622 | 2.907945 |

Discussion. Here we used microarrays to monitor the expression of 22,283 genes as a way to better understand human pluripotential stem cell differentiation. By performing microarrays at multiple time points along their differentiation into bone, muscle, endothelia, and liver, we identified potential processes involved into differentiation into bone, muscle, endothelia, and liver, and also identified a unique signature of genes common to all 4 lineages.

certain matrices may potentially induce a non-specific differentiation, in other words maturation. These matrices, in combination with the lineage specific matrices, have applicability in the development of novel synthetic scaffolds.

Genes that are up-regulated upon differentiation should either be involved in exiting the cell cycle or differentiation (commitment to a particular lineage). Removing the "universally" up-regulated genes allowed us to identify "lineage specific" genes that are not only responsible for differentiation into a particular lineage, but might serve as markers of differentiation. We demonstrate the quality of this data set by clustering this lineage specific data set using Gene Ontology and by identifying tissue specific processes.

A transcriptional signature of stem cells, their progenies and somatic cells will allow for the characterization of unknown/uncommitted progenitor intermediates. For example, in the development of our hepatic differentiation protocol, switching the ECM from matrigel to collagen at day 14, while keeping the same medium formulation, increases the yield of hepatocytes at day 45. The day 14 hepatic intermediate represents an unknown progenitor. Our microarray studies show they have begun differentiation, but do not express hepatic specific markers. Furthermore, clustering of this data set demonstrates that its transcriptional signature is most similar to osteo, therefore representing a meso-endodermal intermediate, and identifies a novel receptor whose targeting might improve the yield of hepatocytes.

Although our data sets consist of numerous unknown or ESTs, we focused our attention on known genes which can be readily targeted for tissue engineering applications. By clustering with gene ontology, we were able to characterize these data sets based on genetic processes, pathways and "drugable targets" (such as receptors, enzymes, signal transducers and nuclear orphan receptors) which can be easily implemented into new differentiation protocols. Genes that were "universally" down-regulated provide insight into unique genes that are enriched in the undifferentiated stage. Targeting of these genes might improve and define the culturing conditions necessary for undifferentiated expansion of human pluripotenital stem cells. Furthermore, the pathways and epigenetic genes in this data set might serve as targets that need to be activated to de-differentiate adult somatic cells like hepatocytes or beta islet cells to an expandable progenitor cell which can then be differentiated and transplanted back into the same patient as therapy. When this data is interpreted in the context of nuclear reprogramming studies that show different cells (embryonic stem cells vs fetal cells vs adult cells) are reprogrammed with different efficiency rates, and this difference is probably due to their epigenetic status, our transcriptional data might provide insight into hotspots within the epigenome that is regulating this pluripotential transcriptional expression. We believe that our transcriptional signatures consist of only a piece of the puzzle, and that "stemness" will also need to be defined at the epigenetic and proteomic level.

This platform has allowed us to target a subset of these lineage specific up-regulated genes or the universally down-regulated genes with small molecule inhibitors and use the universally up-regulated genes as markers to evaluate the quality and quantity of these new protocols. In addition, these data sets provide signatures of in vitro human organogenesis which allows us to study the transcriptional effects of drugs such as ethanol as a way to model human disease.

REFERENCES

1. Thomson J A et al: Embryonic stem cell lines derived from human blastocysts. *Science* 1998, 282:1145-1147.
2. Cibelli J B et al: Parthenogenetic stem cells in nonhuman primates. *Science* 2002, 295:819.
3. Vrana K E et al: Nonhuman primate parthenogenetic stem cells. *Proc Natl Acad Sci U S A* 2003, 100 Suppl 1:11911-11916.
4. Shamblott M J et al.,: Derivation of pluripotent stem cells from cultured human primordial germ cells. *Proc Natl Acad Sci U S A* 1998, 95:13726-13731.
5. D'Amour K A, Gage F H: Genetic and functional differences between multipotent neural and pluripotent embryonic stem cells. *Proc Natl Acad Sci U S A* 2003, 100 Suppl 1:11866-11872.
6. Dvash T et al.: Temporal gene expression during differentiation of human embryonic stem cells and embryoid bodies. *Hum Reprod* 2004, 19:2875-2883.
7. Ivanova N B et al: A stem cell molecular signature. *Science* 2002, 298:601-604.
8. Sato N et al: Molecular signature of human embryonic stem cells and its comparison with the mouse. *Dev Biol* 2003, 260:404-413.
9. Wright L S et al: Gene expression in human neural stem cells: effects of leukemia inhibitory factor.*J Neurochem* 2003, 86:179-195.
10. Li C, Wong W H: Model-based analysis of oligonucleotide arrays: expression index computation and outlier detection. *Proc Natl Acad Sci U S A* 2001, 98:31-36.
11. Irizarry R A et al: Summaries of Affymetrix GeneChip probe level data. *Nucleic Acids Res* 2003, 31:e15.
12. Smyth G K: Linear models and empirical Bayes methods for assessing differential expression in microarray experiments. *Statistical Applications in Genetics and Molecular Biology* 2004, 3.
13. Wettenhall J M, Smyth G K: limmaGUI: a graphical user interface for linear modeling of microarray data. *Bioinformatics* 2004, 20:3705-3706.
14. Lönnstedt I S T: Replicated microarray data. *Statistica Sinica* 2002, 12:31-46.
15. Benjamini Y et al.: Controlling the false discovery rate in behavior genetics research. *Behav Brain Res* 2001, 125: 279-284.
16. Hosack D A et al: Identifying biological themes within lists of genes with EASE. *Genome Biol* 2003, 4:R70.

The foregoing is illustrative of the present invention, and is not to be construed as limiting thereof. The invention is defined by the following claims, with equivalents of the claims to be included therein.

That which is claimed is:

1. A method of screening a human amniotic fluid stem cell for differentiation into a hepatogenic-specific cell line, comprising:
   (a) providing a human amniotic fluid stem cell for which differentiation is to be determined, then
   (b) subjecting said human amniotic fluid stem cell to differentiating conditions; and then
   (c) detecting in said human amniotic fluid stem cell differential expression of at least one hepatogenic specific gene selected from the group consisting of stearoyl CoA desaturase (SCD), and 3-hydroxy-3-methylglutaryl-Coenzyme A reductase (HMGCR),
   wherein upregulation of expression of said at least one hepatogenic specific gene indicates differentiation of said human amniotic fluid stem cell into a hepatogenic specific cell line.

2. The method of claim 1, wherein said detecting step comprises detecting upregulation of expression of at least two hepatogenic specific genes selected from the group consisting of SCD and HMGCR;
   wherein upregulation of said at least two hepatogenic specific genes indicates differentiation of said human amniotic fluid stem cell into a hepatogenic specific cell line.

3. The method of claim 1, wherein does said amniotic fluid stem cell does not form a teratoma when grown in vivo.

4. The method of claim 1, wherein said amniotic fluid stem cell does not form a teratoma within one month after intraarterial injection into a 6-8 week old mouse at a dose of $5 \times 10^6$ cells per mouse.

5. The method of claim 1, wherein said amniotic fluid stem cells are isolated from amniotic fluid between 14 and 18 weeks of gestation.

6. The method of claim 1, wherein said detecting step comprises detecting in said human amniotic fluid stem cell differential expression of stearoyl CoA desaturase (SCD).

7. The method of claim 1, wherein said detecting step comprises detecting in said human amniotic fluid stem cell differential expression of 3-hydroxy-3-methylglutaryl-Coenzyme A reductase (HMGCR).

* * * * *

UNITED STATES PATENT AND TRADEMARK OFFICE
CERTIFICATE OF CORRECTION

| | | |
|---|---|---|
| PATENT NO. | : 7,883,847 B2 | Page 1 of 1 |
| APPLICATION NO. | : 11/394766 | |
| DATED | : February 8, 2011 | |
| INVENTOR(S) | : Hipp et al. | |

It is certified that error appears in the above-identified patent and that said Letters Patent is hereby corrected as shown below:

On the Title Page:
Item (56), References Cited, Right Column, Line 21, Gomez F E et al.:
    correct "5473-5452" to read -- 5473-5482 --

Right Column, Line 33, Ginis I et al:
    correct "269-380" to read -- 269: 360-380 --

Column 4, Line 46: correct "4 (TIP4)" to read -- 4 (TIMP4) --

Column 7, Line 40: correct "1 M" to read -- 1 µM --
    Line 47: correct "(110M," to read -- (10µM, --

Column 8, Line 14: correct "for Oct. 4," to read -- for Oct4 --

In the Claims:
Column 23, Claim 3, Line 1: correct "wherein does said"
    to read -- wherein said --

Signed and Sealed this
Sixteenth Day of August, 2011

David J. Kappos
*Director of the United States Patent and Trademark Office*